United States Patent
Fieselmann (10) Patent No.: US 10,319,117 B2
(45) Date of Patent: Jun. 11, 2019

(54) RECORD AND RECONSTRUCT X-RAY IMAGE DATA ON THE BASIS OF ELLIPTICAL CYLINDERS

(71) Applicant: SIEMENS HEALTHCARE GMBH, Erlangen (DE)

(72) Inventor: Andreas Fieselmann, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 218 days.

(21) Appl. No.: 15/497,424

(22) Filed: Apr. 26, 2017

(65) Prior Publication Data
US 2017/0309044 A1 Oct. 26, 2017

(30) Foreign Application Priority Data
Apr. 26, 2016 (DE) .................. 10 2016 207 064

(51) Int. Cl.
| | |
|---|---|
| G06T 11/00 | (2006.01) |
| A61B 6/02 | (2006.01) |
| A61B 6/00 | (2006.01) |
| G06T 7/00 | (2017.01) |
| G06T 7/11 | (2017.01) |

(52) U.S. Cl.
CPC .......... *G06T 11/003* (2013.01); *A61B 6/022* (2013.01); *A61B 6/505* (2013.01); *G06T 7/0012* (2013.01); *G06T 7/11* (2017.01); *G06T 2207/10116* (2013.01); *G06T 2210/41* (2013.01)

(58) Field of Classification Search
USPC ........................................ 382/128, 131, 132
See application file for complete search history.

(56) References Cited

U.S. PATENT DOCUMENTS

| | | | |
|---|---|---|---|
| 6,778,630 B2* | 8/2004 | Silver ................. | G06T 11/005 378/15 |
| 7,073,939 B2* | 7/2006 | Spahn ................. | A61B 6/488 378/189 |
| 9,582,940 B2 | 2/2017 | Yu et al. | |
| 2003/0123614 A1* | 7/2003 | Silver ................. | G06T 11/005 378/146 |
| 2003/0128801 A1* | 7/2003 | Eisenberg ........... | A61B 6/032 378/19 |

(Continued)

FOREIGN PATENT DOCUMENTS

| | | |
|---|---|---|
| JP | H08289888 A | 11/1996 |
| WO | 2016045574 A1 | 3/2016 |

OTHER PUBLICATIONS

Heuscher, D. et al: "CT Dose Reduction Using Dynamic Collimation", IEEE Nuclear Science Symposium and Medical Imaging Conference (NSS/MIC), 2011, pp. 3470-3473, 2011.

(Continued)

*Primary Examiner* — Ishrat I Sherali
(74) *Attorney, Agent, or Firm* — Laurence Greenberg; Werner Stemer; Ralph Locher (57) ABSTRACT

A recording and reconstruction of image data of a predetermined object of an examination object is performed by an x-ray system. The x-ray system determines a number of elliptical cylinders so that the object is arranged entirely in the volumes of the cylinders. Data within each of the cylinders is recorded by the x-ray system. The image data of the object is reconstructed based on the data recorded for each of the cylinders.

12 Claims, 4 Drawing Sheets

(56) References Cited

U.S. PATENT DOCUMENTS

2004/0240609 A1   12/2004   Spahn
2017/0336334 A1*  11/2017   Yun ...................... G01N 23/223
2018/0228452 A1*   8/2018   Badal-Soler ........... A61B 6/032

OTHER PUBLICATIONS

Xia, Y. et al.: "Patient-bounded extrapolation using low-dose priors for volume-of-interest imaging in C-arm CT", Medical Physics, vol. 42, pp. 1787-1796, 2015.
Shaw, C: "Volume-of-Interest Cone Beam CT", Cone Beam Computed Tomography, CRC S.115-122, Press, 2014.
Humbert et al.: "3D reconstruction of the spine from biplanar X-rays using parametric models based on transversal and longitudinal inferences", Medical Engineering & Physics, 31:681-7, 2009.

* cited by examiner

FIG 4

FIG 5 dow, an x-ray system. The inventive method contains the following below described steps:

RECORD AND RECONSTRUCT X-RAY IMAGE DATA ON THE BASIS OF ELLIPTICAL CYLINDERS

CROSS-REFERENCE TO RELATED APPLICATION

This application claims the priority, under 35 U.S.C. § 119, of German application DE 10 2016 207 064.9, filed Apr. 26, 2016; the prior application is herewith incorporated by reference in its entirety.

BACKGROUND OF THE INVENTION

Field of the Invention

The present invention relates to the recording and reconstruction of image data of a predetermined object within an examination object with the aid of an x-ray system.

Published, Japanese patent application JP H08-289 888 A discloses a tomography system, which, based on a plan, records data from various slices of a spinal column.

International patent disclosure WO 2016/045 574 A1, corresponding to U.S. Pat. No. 9,582,940, describes a combination of three-dimensional partial images which were recorded beforehand with an x-ray system.

In the article entitled "CT Dose Reduction Using Dynamic Collimation", by D. J. Heuscher, Nuclear Science Symposium and Medical Imaging Conference (NSS/MIC), 2011 IEEE, pages 3470 to 3473, a collimator is used in a CT scan so that an x-ray dose is significantly reduced.

U.S. patent publication 2004/0240609 A1 describes the creation of x-ray recordings along a curved course, in order then to combine these recordings to form an overall image.

The recording of image data of the spinal column by computed tomography is a known method for assessing scoliosis or spinal canal stenosis. In such cases a computed tomography system records images of the spinal column in the horizontal or vertical position of the patient, wherein three-dimensional x-ray recordings are created. Furthermore, two-dimensional recordings of the spinal column in the vertical position of the patient can be recorded by radiography. The creation of x-ray recordings in the natural vertical position of the patient offers diagnostic advantages here.

Attempts are made here to keep the dose of x-rays to which the patient is exposed during the recording of x-ray data as low as possible, especially with children. A known technique for reducing the x-ray dose in digital volume tomography ("Cone beam" CT (CBCT)) is the use of a collimator, in order, as far as possible, only to irradiate the volume of the patient to be scanned while the x-ray data is being recorded. Numerous approaches exist here to attenuate or avoid artifacts during the image construction if a collimated scanning has been used.

A conventional x-ray source only supports a rectangular collimation of the x-ray beam. Therefore when a collimation according to the prior art is used, the scanned volume has in most cases the shape of a cylinder. However, even with healthy patients the spinal column is slightly S-shaped, wherein this S-shape has more enhanced characteristics in patients with scoliosis for instance. On account of this S-shape of the spinal column, a cylinder is not an optimal shape in order to keep the dose of x-rays as low as possible while recording x-ray data of the spinal column.

SUMMARY OF THE INVENTION

The object of the present invention is therefore to optimize the recording and reconstruction of image data of an object, in particular a human spinal column, so that the dose of x-rays which is required for this and to which the patient is exposed is lower than in accordance with the prior art.

In accordance with the invention, this object is achieved by a method for recording and reconstructing image data of a predetermined object of an examination object by means of an x-ray system, by an x-ray system, by a computer program product and by an electronically readable data carrier. The dependent claims define preferred and advantageous embodiments of the present invention.

Within the scope of the present invention, there is provision for a method for recording and reconstructing image data of a predetermined object (in particular of a predetermined organ, e.g. the spinal column) of a living examination object by use of an x-ray system. The inventive method contains the following below described steps:

0) Determining a number of elliptical cylinders such that the object is disposed entirely in the collective volume of the elliptical cylinders. If, in other words, the volumes of the elliptical cylinders are combined or merged to form an overall volume, the object is disposed entirely within this overall volume.

b) Recording x-ray data of each of the elliptical cylinders with the aid of the x-ray system (i.e. x-ray data is recorded within each cylinder). In other words, x-ray data is recorded for each or from each cylinder, or more precisely x-ray data is recorded within volumes which correspond to the cylinders. In such cases the x-ray data of the cylinders is recorded in particular in separate steps for the respective cylinder. This means that especially primarily the x-ray data is only recorded within a first of the cylinders and then within a second of the cylinders etc. until the x-ray data of all cylinders has been recorded. The x-ray data is recorded here in particular from different angles, as is explained in more detail below.

c) Reconstruction of the image data of the object on the basis of x-ray data recorded for each cylinder.

Since a single cylinder which is adjusted in respect of its dimensions such that the object to be recorded is disposed in its volume generally has a larger volume than if a number of cylinders are used which are adjusted in each case to specific segments of the object, the radiation exposure of the patient, which is proportional to the volume to be recorded, can be reduced if only the data of the cylinders is recorded, as is the case in accordance with the invention. In other words, a number of cylinders can be better adjusted (i.e. with a lower overall volume) to any object, for instance a human spinal column, than is the case with just one cylinder.

An elliptical cylinder is understood here to mean a cylinder whose surface at right angles to the central axis of the cylinder corresponds to an ellipse. Here a cylinder whose surface at right angles to the central axis corresponds to a circle is regarded as the special case of the elliptical cylinder.

If it is described below that (x-ray) data of a cylinder is recorded, this is understood to mean that the data is recorded within a volume which corresponds to the respective cylinder.

In such cases when the x-ray data of a specific one of the elliptical cylinders is recorded, the x-ray data of this cylinder is recorded with a collimator of the x-ray system.

In such cases the collimator is set for the respective cylinder such that an angle at which x-rays are emitted from an x-ray source of the x-ray system is selected as a function of the dimensions of this cylinder. The x-ray data of this cylinder is only recorded here on the basis of x-rays which are emitted at this specific angle.

In other words, the collimator is set for the respective cylinder such that the x-rays only radiate through the respective cylinder (and inevitably regions in front of and behind this cylinder), but not regions laterally adjacent to the cylinder.

In such cases the x-ray system can be moved about the examination object and thus about the object to be recorded, wherein in each position the x-rays emitted by the x-ray system fulfill the afore-described angle condition.

The angle at which the x-rays are emitted is selected here in particular so that an x-ray beam on a first side of the angle radiates through a first boundary of the respective cylinder and that an x-ray beam on a second side of the angle radiates through a second boundary of the respective cylinder.

In other words, the angle is advantageously selected such that the respective cylinder is only just disposed within this angle.

According to another preferred inventive embodiment, the recording of the x-ray data of each of the cylinders for the respective cylinder contains the following steps:
a) determining a scan plane which is arranged at right angles to a longitudinal central axis of the respective cylinder and intersects the respective cylinder;
b) determining an ellipse which lies within the previously determined scan plane and whose periphery is disposed in the lateral area of the respective cylinder;
c) determining as large an angle as possible in the scan plane, at which the x-rays are emitted from the x-ray source, wherein each of the two sides of this angle intersect with the periphery of the ellipse; and
d) recording the x-ray data of the respective cylinder, wherein in order to record this x-ray data the x-rays are only emitted at the specific angle.

In accordance with the invention, in order to record the x-ray data of the respective cylinder, it is possible to repeatedly carry out the steps of determining the largest possible angle and recording the x-ray data of the respective cylinder by rotating the x-ray source about the examination object and thus about the object to be recorded.

The x-ray data of a specific cylinder can be recorded in slices for instance, by the x-ray data being recorded slice by slice, wherein each slice lies at right angles to the central axis of the cylinder. In this case the afore-described angle is a two-dimensional angle.

However, it is also possible to set the collimator such that the x-rays radiate through the entire cylinder. In this case the collimator is set in accordance with a dihedral angle, the boundaries of which are defined by the dimensions of the cylinder.

The determination of the number of elliptical cylinders can comprise the following steps:
a) subdividing the object into a number of segments, wherein the totality of these segments produces the object (i.e. there is no part of the object which does not belong to a segment);
b) assigning respectively an elliptical cylinder to one of the previously determined segments; and
c) adjusting the respective cylinder to the dimensions of the segment previously assigned to it. In such cases the assigned segment must be arranged entirely within the cylinder and the volume of the cylinder is to be as small as possible.

The subdivision of the object into the number of segments is performed here in particular such that a cylinder can be adjusted as well as possible to the respective segment. In this case a cylinder can then be adjusted as well as possible to the respective segment, if the respective segment itself virtually has the shape of a cylinder.

If the object has an extent in a longitudinal direction of the object which is greater than an extent in a width direction or than an extent in a height direction of the object (i.e. it is an oblong object), the subdivision of the object into the number of segments can be performed as now described.

One or a number of points in the object is/are determined, at which a central line of the object which runs substantially in the longitudinal direction of the object has a bend, wherein this bend in turn has an angle which is larger than a predetermined angle threshold value. In this embodiment two of the segments, into which the object is to be subdivided, end at each point at which the previously described condition is fulfilled.

The previously described embodiment is particularly suited to objects which are composed of a number of segments which run substantially in a straight line in each case, wherein the central lines or central axes of the respective segments have the said bend with respect to one another. One example of such an object is the human spinal column.

According to a preferred inventive embodiment, two overview x-ray images are recorded and/or created with the aid of the x-ray system. The predetermined object (e.g. the human spinal column) can then be segmented on the basis of these overview x-ray images.

This segmentation of the object can be performed here fully automatically or also purely manually or semi-automatically.

In accordance with the invention it is possible for the image data of the object that is recorded and reconstructed in accordance with the present invention to be combined with the two overview x-ray images.

An observer can be given a good overview by the two overview x-ray images which are created from the x-ray data recorded beforehand on the basis of the cylinders being superimposed onto the three-dimensional image data of the object for instance.

Within the scope of the present invention, there is also provision for an x-ray system, which contains a detector, an x-ray source for emitting x-rays directed onto the detector, a controller for controlling the x-ray source and the detector and an image computing unit for receiving x-ray data recorded by the detector. In such cases the x-ray system is configured such that the x-ray system records and reconstructs image data of a predetermined object of an examination object. Here the x-ray system is configured in order to determine a number of elliptical cylinders so that the object is disposed entirely in the volumes of these cylinders, in order to record x-ray data for each of these cylinders and with the aid of the image computing unit in order to reconstruct the image data of the object as a function of this x-ray data recorded for each of the cylinders.

The advantages of the inventive x-ray system correspond substantially to the advantages of the inventive method, which are cited above in detail, so that a repetition is omitted here.

Furthermore the present invention describes a computer program product, in particular a computer program or a software, which can be loaded into a memory of a programmable controller or of a computing unit of an x-ray system. This computer program product can be used to carry out all or various previously described embodiments of the inventive method, if the computer program product runs in the controller or control device of the x-ray system. In such cases the computer program product requires possible program means, e.g. libraries and auxiliary functions, in order to realize the corresponding embodiments of the method. In other words, a computer program or software is in particular to be protected by the claim focusing on the computer program product, with which one of the above-described embodiments of the inventive method can be carried out or which carries out this embodiment. Here, the software may be a source code (e.g. C++) which must still be compiled (translated) and linked or which only has to be interpreted, or an executable software code, which for execution purposes only has to be loaded into the corresponding computing unit.

Finally, the present invention discloses an electronically readable data carrier, e.g. a DVD, a magnetic tape, a hard disk or a USB stick, on which electronically readable control information, in particular software (cf. above), is stored. If this control information (software) is read from the data carrier and stored in a controller or computing unit of an x-ray system, all inventive embodiments of the above-described method can be performed.

The present invention has the now described advantages compared to the prior art:
a) The radiation dose to which the patient is exposed in order to record x-ray data is lower due to a more effective collimation, since a lower volume is to be irradiated. The most significant reduction in respect of radiation exposure can be achieved here if the entire spinal column is scanned. However, compared with the prior art a lower radiation exposure is also achieved if only one part of the spinal column is scanned.
b) Combining the overview images with the image data, which is reconstructed based on the x-ray data recorded for the cylinders, assists an observer with interpreting the image data.
c) The present invention can be used for a three-dimensional imaging of the spinal column irrespective of whether the x-ray data of a horizontal or a vertical patient is recorded. In such cases the present invention permits the reconstruction of a true tomographic three-dimensional volume of the spinal column.

Other features which are considered as characteristic for the invention are set forth in the appended claims.

Although the invention is illustrated and described herein as embodied in a record and reconstruct x-ray image data on the basis of elliptical cylinders, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
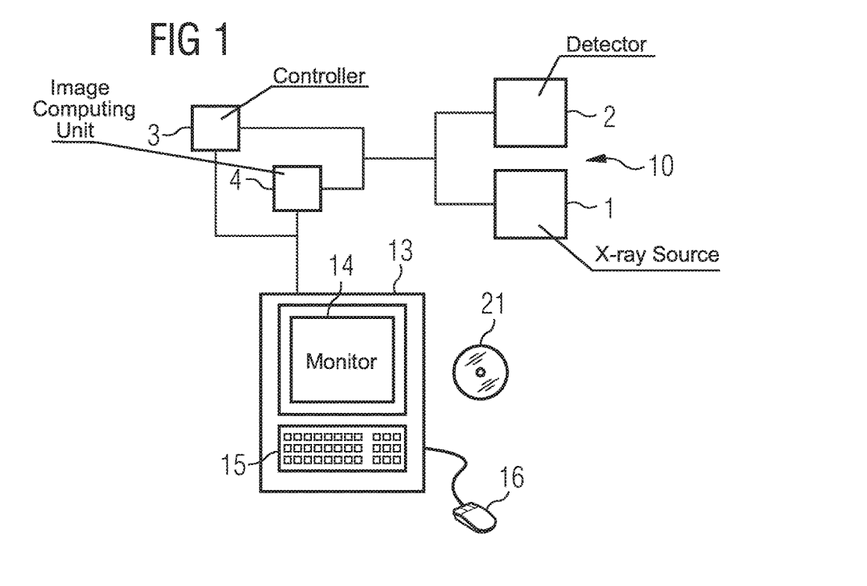
FIG. 1 is a schematic representation of an x-ray system according to the invention.

Referring now to the figures of the drawings in detail and first, particularly to FIG. 1 thereof, there is shown a schematic representation of an inventive x-ray system. Aside from an x-ray source 1 and a detector 2, the x-ray system has a controller 3, an image computing unit 4 and a terminal 13 with a monitor 14, a keyboard 15 and a mouse 16. The controller 3 controls both the x-ray source 1 and also the detector 2. X-ray data which is recorded by way of the detector 2 is fed to the image computing unit 4, wherein based on this x-ray data the image computing unit 4 then reconstructs image data which is then shown on the monitor 14 for instance. Control programs, on the basis of which the present invention can be carried out, can be disposed on the data carrier or the DVD 21, wherein these control programs are then loaded into the controller 3 in order to carry out the present invention.

Figure 2:
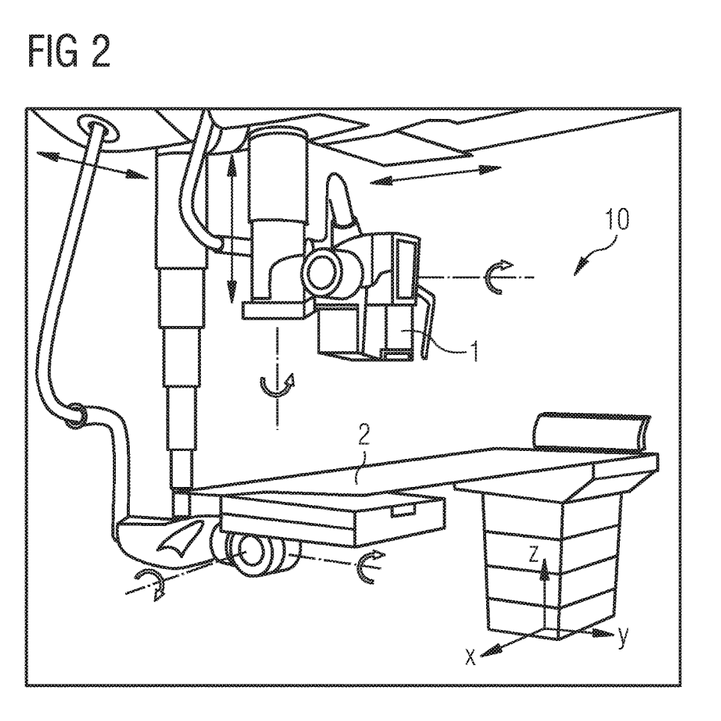
FIG. 2 is a diagrammatic, perspective view of a twin robotic x-ray scanner.

FIG. 2 shows an inventive twin robotic x-ray scanner 10 as an inventive x-ray system 10. With this x-ray scanner 10, both the x-ray source 1 and also the detector 2 can be rotated in each case about a number of axes and can be moved in each case along at least one spatial direction. The inventive robot-controlled x-ray scanner 10 permits the recording and reconstruction of three-dimensional image data with just one patient positioning, by the x-ray source 1 and the detector 2 moving in a coordinated manner about the patient.

The present invention is to be explained below with the aid of FIGS. 3A-3G.

With the aid of the x-ray system 10, in the present case in a first step two or more x-ray images or fluoroscopes of the spinal column of the examination object O or of the patient are created with a low radiation dose. These two overview images 11, 12 are generally created in two lines of sight which are vertical to one another (i.e. the directions in which the x-rays for creating the two overview images 11, 12 are emitted, are substantially vertical to one another). In such cases the overview images 11, 12 must have the axial length of the planned three-dimensional overview image (in the present case the axial length corresponds to the length of the spinal column to be recorded). In order to create this, the x-ray system 10 shown in FIG. 2 is used, in which the x-ray source 1 and detector 2 are automatically tilted so that the afore-cited directions are vertical to one another.

It should be noted that in order to create a normal three-dimensional overview image (3D scan), two fluoroscopes with directions which are vertical to one another (see above) must generally be created. In other words, these overview images recorded anyway in accordance with the prior art can be used for the present invention. Additional overview images must only be recorded with a low radiation dose if the axial length with these overview images is not sufficient (since the spinal column to be recorded is longer).

In a next step a simple three-dimensional model of the spinal column 5 is segmented based on the two overview images 11, 12.

A number of elliptical cylinders (see FIG. 4) are then adjusted to the three-dimensional spinal column model using the following conditions. The first condition is that the volume of the cylinders is as small as possible in each case. The second condition is that the spinal column or the spinal column model is arranged entirely in the cylinders. In other words, the spinal column must be disposed entirely in an overall volume, which is composed of the volumes of the individual cylinders. A cylinder number is predetermined as the third condition, wherein the number of cylinders is not permitted to exceed this cylinder number. The method for determining the elliptical cylinders can be implemented as an optimization method.

In order to determine the elliptical cylinders which generally overlap, the spinal column 5 can be subdivided into various segments 31-33 for instance, wherein a respective cylinder 41-43 is then adjusted to each segment 31-33.

The scan parameters can then be determined as a function of the cylinders 41-43, in order then to record the x-ray data of the respective cylinder 41-43 with these scan parameters.

To this end a scan plane 51-53 which is at right angles to the central axis of the respective cylinder 41-43 is determined for each cylinder 41-43 for instance. The center (within the cylinder 41-43) can then be determined for the respective scan plane 51-53. Projection-dependent collimator settings can then be determined as part of the scan parameters on the basis of the cylinder 41-43, the scan plane 51-53 and the central point.

Parameters for each axis of the inventive x-ray system 10 shown in FIG. 2 can then be determined based on the scan parameters, wherein an inverse kinematic algorithm is generally used.

The corresponding scan parameters and parameters of the x-ray system 10 are then used to record x-ray data for each cylinder 41-43. Image data or a 3D x-ray image 17 is then reconstructed based on this x-ray data. In such cases algorithms can be used to reduce or as far as possible completely avoid artifacts which may occur with segmented x-ray data.

The three-dimensional x-ray image 17 can optionally be fused with one or with both overview images 11, 12, in order to offer a better overview to a radiologist in particular, wherein the x-ray image 18 is produced as a result. To this end one or both x-ray images 11, 12 can be superimposed onto the three-dimensional x-ray image 17 as a corresponding projection.

Figure 4:
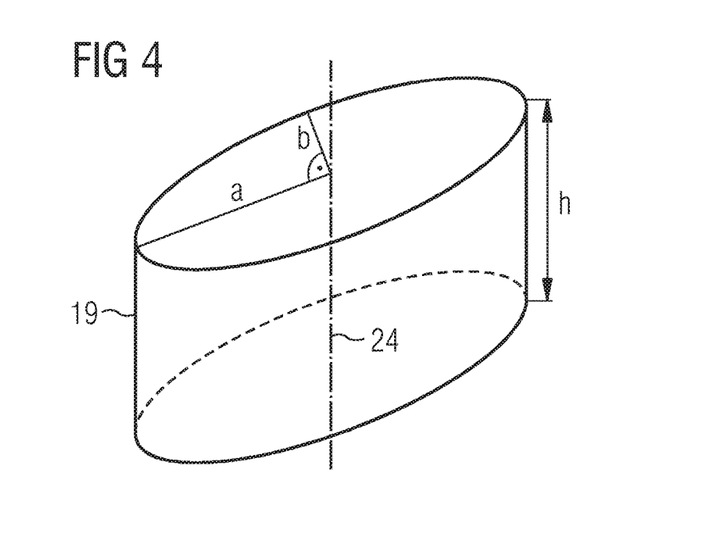
FIG. 4 is an illustration of an elliptical cylinder.

An elliptical cylinder 19 is shown by way of example in FIG. 4. This elliptical cylinder 19 has a central axis 24 and a height h. The intersecting plane at right angles to the central axis 24 has in each case the shape of an ellipse, wherein in FIG. 4 the length of the large semi-axis of this ellipse is identified with the reference character a and the length of the small semi-axis of this ellipse is identified with the reference character b.

Figure 5:
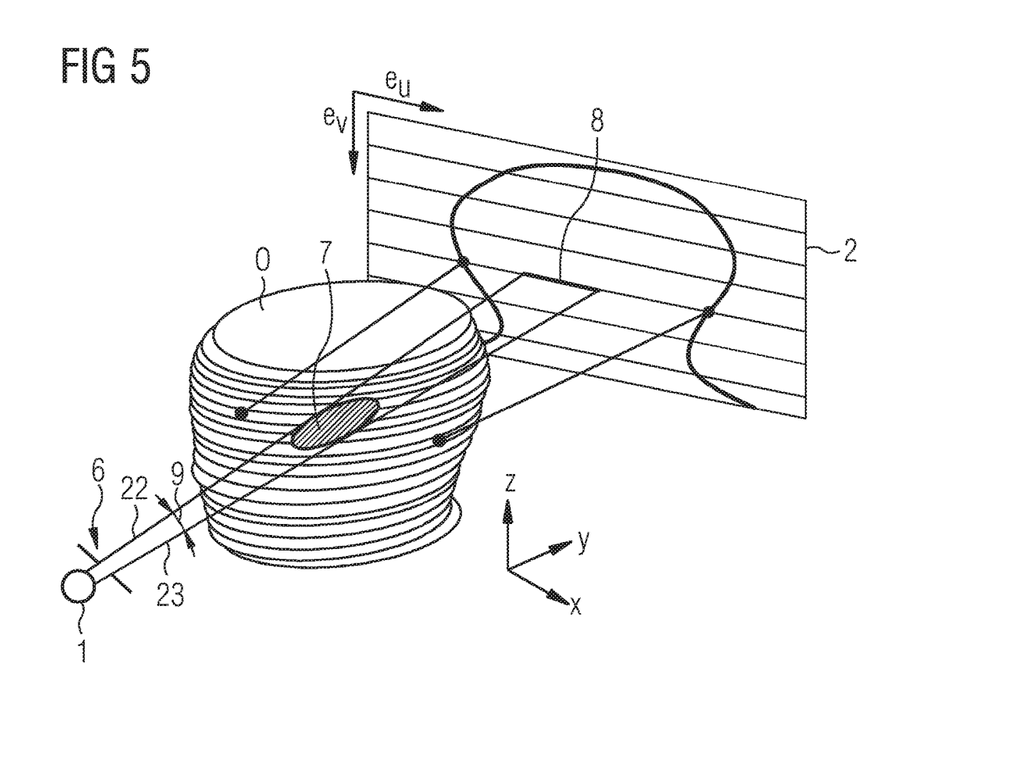
FIG. 5 is an illustration showing an inventive determination of an angle, at which x-rays are radiated.

The setting of a collimator 6 of the inventive x-ray system is to be explained with FIG. 5. An elliptical cylinder (not shown in FIG. 5), of or in which a specific slice is to be recorded with the collimator setting shown in FIG. 5, is disposed within the examination object O. This slice, which is at right angles to the central axis of the cylinder, is represented by an ellipse 7. In order only to radiate through this ellipse 7 with x-rays (and not other regions of the slice or plane at right angles to the central axis), the collimator 6 is set such that the x-rays are only emitted at a specific angle 9.

The dimensions of the angle 9 are selected such that the two sides 22, 23 of the angle 9 are straight tangent to the periphery of the ellipse 7. The projection 8 on the detector 2 is produced with the corresponding collimator setting (in particular angle 9).

Figure 6:
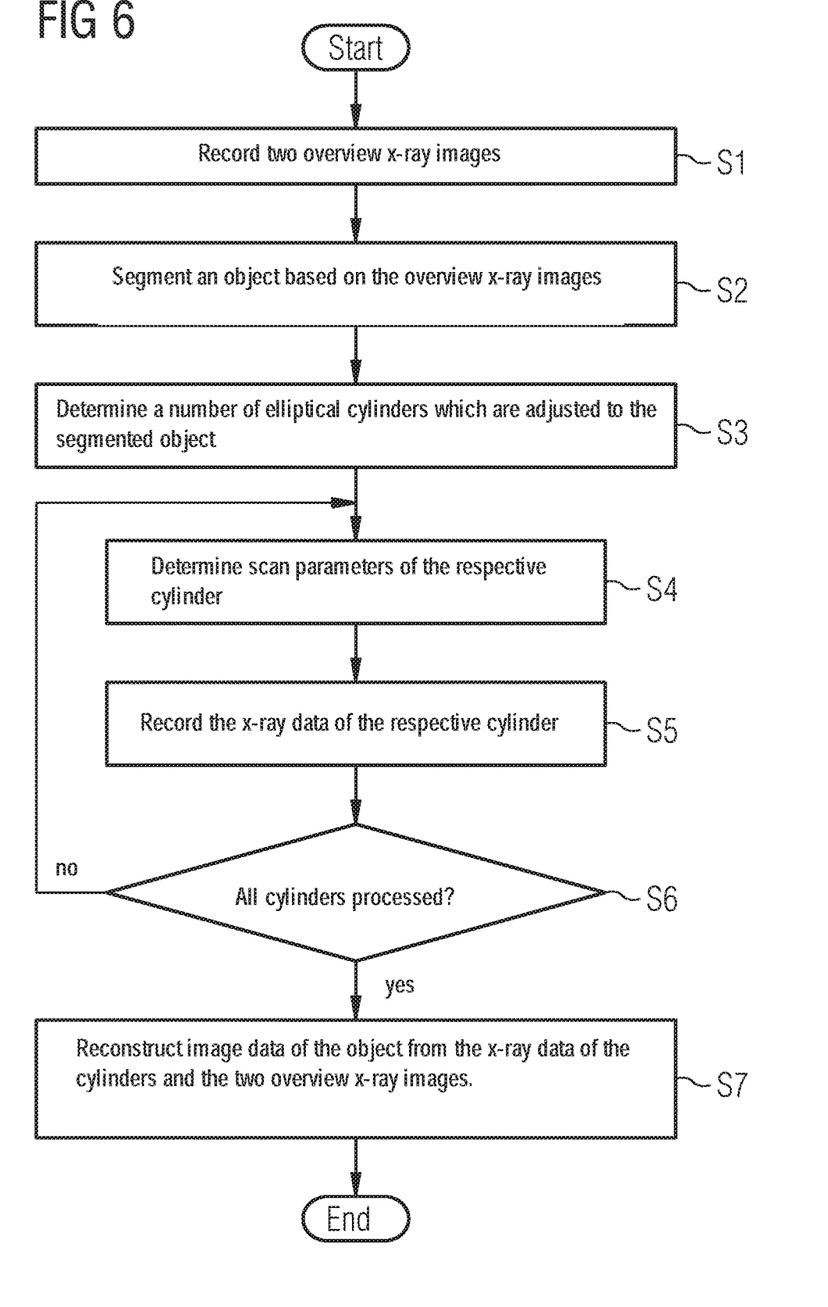
FIG. 6 is a flow chart for explaining a method according to the invention.

A flow chart of the inventive method is shown in FIG. 6.

Figure 3:
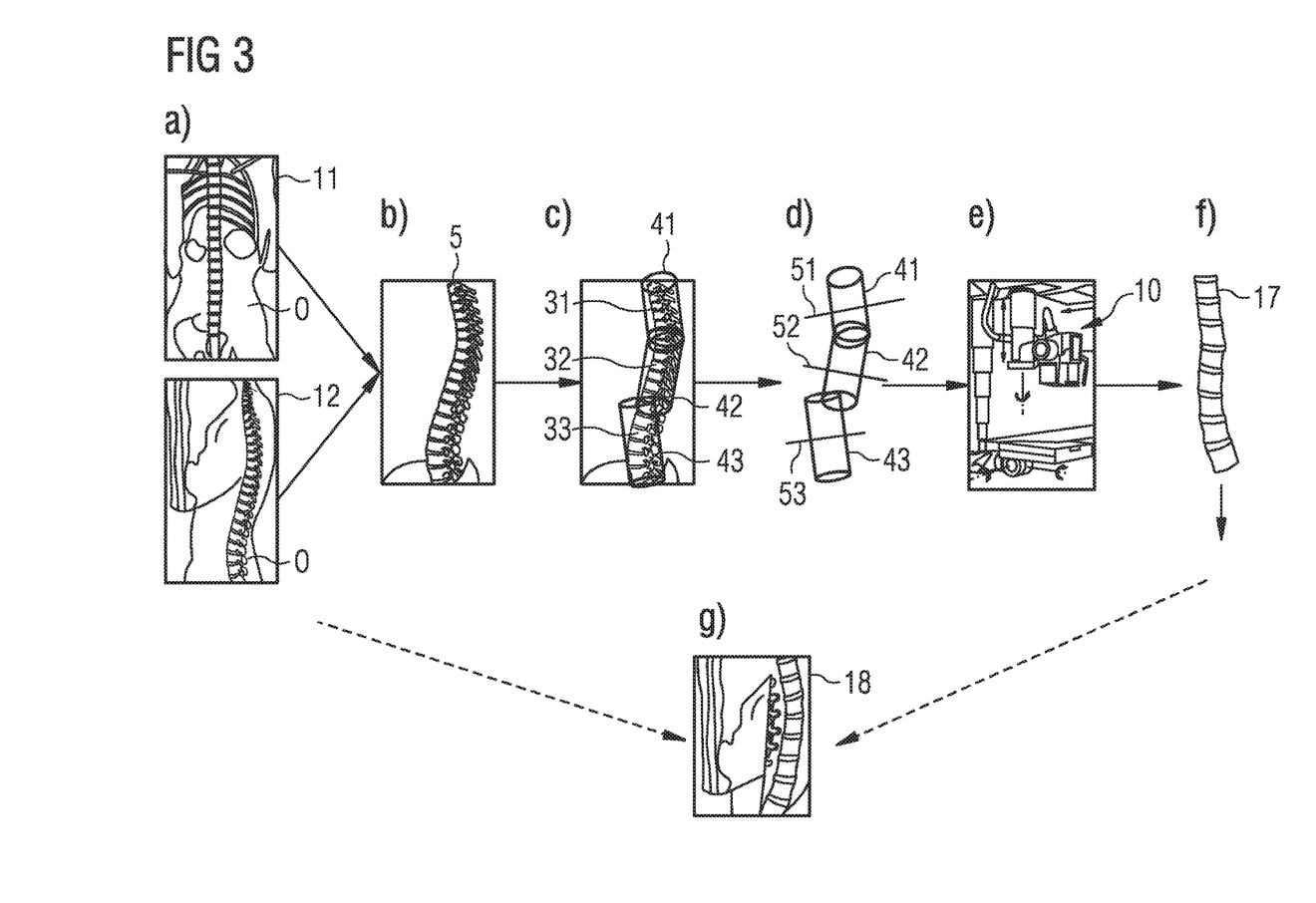
FIGS. 3A-3G are illustrations showing sequences of the present invention in the form of individual images.

In a first step S1, the two overview x-ray images 11, 12 are recorded, FIG. 3A. On the basis of these two overview x-ray images 11, 12, a three-dimensional model of the segment of the examination object O, in which the object 5 to be examined is disposed, can be created, FIG. 3B. Therefore in step S2 the object 5 can be segmented based on the overview x-ray images 11, 12.

In the following step S3, a number of elliptical cylinders 41-43 is determined, which are produced such that they are adjusted as optimally as possible to the segmented object 5, FIG. 3C.

The two following steps S4 and S5 are now embodied for each of the previously determined cylinders 41-43. In step S4, the scan parameters (e.g. the collimator settings) are determined for the respective cylinders, FIG. 3D. The x-ray data of the respective cylinder is then recorded with the scan parameters determined in step S4, FIG. 3E. The inventive method only moves to step S7 if it is decided in step S6 that steps S4 and S5 have been carried out for all cylinders. In this step S7, image data of the object to be examined is reconstructed on the basis of the x-ray data recorded previously for each cylinder 41-43 and optionally additionally from the two overview x-ray images 11, 12.

The following is a summary list of reference numerals and the corresponding structure used in the above description of the invention:

1 X-ray source
2 Detector
3 Controller
4 Image computing unit
5 Spinal column
6 Collimator
7 Ellipse
8 Projection
9 Angle
10 X-ray system
11 Overview image
12 Overview image
13 Terminal
14 Monitor
15 Keyboard
16 Mouse
17,18 3D x-ray image
19 Cylinder
21 DVD
22,23 Side of the angle
24 Central axis
31-33 Segment
41-43 Cylinder
51-53 Scan plane
a Length of the large semi-axis
b Length of the small semi-axis
h Height
O Examination object
S1-S7 Method step

The invention claimed is:

1. A method for recording and reconstructing image data of a predetermined object of an examination object by means of an x-ray system, which comprises the following steps of:

determining a number of elliptical cylinders so that the predetermined object is disposed entirely in volumes of the elliptical cylinders;

recording data within each of the elliptical cylinders by means of the x-ray system, wherein when the data within each of the elliptical cylinders is recorded for each of the elliptical cylinders, a collimator of the x-ray system is set such that a specific angle, at which x-rays are emitted from an x-ray source of the x-ray system, is selected in dependence on dimensions of a respective cylinder, and the data within the respective cylinder is recorded with the x-rays which are only emitted at the specific angle; and reconstructing the image data of the predetermined object based on the data recorded for each of the elliptical cylinders.

2. The method according to claim 1, which further comprises selecting the specific angle such that an x-ray beam on a first side of the specific angle radiates through a first boundary of the respective cylinder and that an x-ray beam on a second side of the specific angle radiates through a second boundary of the respective cylinder.

3. The method according to claim 1, wherein the recording of the data within each of the elliptical cylinders for each of the elliptical cylinders further comprises the following steps:

determining a scan plane, which is at right angles to a longitudinal central axis of the respective cylinder and runs through the respective cylinder;

determining an ellipse, which lies in the scan plane and whose periphery lies in a lateral area of the respective cylinder;

determining a maximum set angle in the scan plane, at which the x-rays are emitted from the x-ray source of the x-ray system and whose two sides intersect with the periphery of the ellipse; and recording the data within the respective cylinder, wherein the x-rays are only irradiated at the specific angle.

4. The method according to claim 1, wherein the step of determining the number of elliptical cylinders further comprises:

subdividing the predetermined object into a number of segments;

assigning one of the elliptical cylinders to a specific segment in each case; and adjusting the respective cylinder to dimensions of a segment assigned thereto so that the segment lies entirely within the respective cylinder and the respective cylinder has a minimal volume.

5. The method according to claim 4, which further comprises:

forming the predetermined object such that the predetermined object has an extent in a longitudinal direction, which is larger than an extent in a width direction or than an extent in a height direction of the predetermined object; and determining at least one point in the predetermined object, at which a central line of the predetermined object that runs substantially in the longitudinal direction has a bend which has an angle which is larger than a predetermined angle threshold value, and two of the segments end at each of the at least one point.

6. The method according to claim 1, wherein the predetermined object includes a spinal column of the examination object.

7. The method according to claim 1, which further comprises:

recording two overview x-ray images by means of the x-ray system; and segmenting the predetermined object on a basis of the overview x-ray images.

8. The method according to claim 7, which further comprises combining the reconstructed image data of the predetermined object with the two overview x-ray images.

9. An x-ray system, comprising:
a detector;
an x-ray source for emitting x-rays directed onto said detector;
a controller for controlling said x-ray source and said detector;
an image computing unit for receiving data recorded by said detector;
a collimator; and
the x-ray system being configured to record and reconstruct image data of a predetermined object of an examination object, by the x-ray system determining a number of elliptical cylinders so that the predetermined object is disposed entirely in volumes of the elliptical cylinders, by the x-ray system recording data within each of the elliptical cylinders, and based on the data recorded for each of the elliptical cylinders, by the x-ray system reconstructing the image data of the predetermined object by means of said image computing unit, wherein the x-ray system is configured, during the recording of the data within each of the elliptical cylinders for each of the elliptical cylinders, to set said collimator of the x-ray system such that a specific angle, at which x-rays are irradiated from said x-ray source, is selected in dependence on dimensions of a respective cylinder, and in order to record the data within the respective cylinder with the x-rays which are only emitted at the specific angle.

10. The x-ray system according to claim 9, wherein the x-ray system includes a controller configured to:

determine a number of elliptical cylinders so that the predetermined object is disposed entirely in volumes of the elliptical cylinders;

record data within each of the elliptical cylinders by means of the x-ray system, wherein when the data within each of the elliptical cylinders is recorded for each of the elliptical cylinders, a collimator of the x-ray system is set such that a specific angle, at which x-rays are emitted from an x-ray source of the x-ray system, is selected in dependence on dimensions of a respective cylinder, and the data within the respective cylinder is recorded with the x-rays which are only emitted at the specific angle; and reconstruct the image data of the predetermined object based on the data recorded for each of the elliptical cylinders.

11. A computer program loadable directly into a non-transitory memory of a programmable controller of an x-ray system, the computer program having program instruction for executing all steps of the method according to claim 1, when the computer program is executed in a controller of the x-ray system.

12. An electronically readable non-transitory data carrier with electronically readable control information stored thereupon, said control information configuring a controller to:

determine a number of elliptical cylinders so that the predetermined object is disposed entirely in volumes of the elliptical cylinders;

record data within each of the elliptical cylinders by means of an x-ray system, wherein when the data within each of the elliptical cylinders is recorded for each of the elliptical cylinders, a collimator of the x-ray system is set such that a specific angle, at which x-rays are emitted from an x-ray source of the x-ray system, is selected in dependence on dimensions of a respective cylinder, and the data within the respective cylinder is recorded with the x-rays which are only emitted at the specific angle; and reconstruct the image data of the predetermined object based on the data recorded for each of the elliptical cylinders.

* * * * *